US010890551B2

(12) United States Patent
Oba et al.

(10) Patent No.: US 10,890,551 B2
(45) Date of Patent: Jan. 12, 2021

(54) GAS SENSOR AND METHOD FOR MANUFACTURING THE SAME

(71) Applicant: NGK Spark Plug Co., LTD., Nagoya (JP)

(72) Inventors: Takehiro Oba, Konan (JP); Shogo Nagata, Komaki (JP); Shunya Mihara, Komaki (JP)

(73) Assignee: NGK Spark Plug Co., LTD., Nagoya (JP)

(*) Notice: Subject to any disclaimer, the term of this patent is extended or adjusted under 35 U.S.C. 154(b) by 160 days.

(21) Appl. No.: 15/642,130

(22) Filed: Jul. 5, 2017

(65) Prior Publication Data
US 2018/0011047 A1 Jan. 11, 2018

(30) Foreign Application Priority Data

Jul. 7, 2016 (JP) .................................. 2016-135101
Jun. 30, 2017 (JP) .................................. 2017-128371

(51) Int. Cl.
*G01N 27/406* (2006.01)
*H01R 43/20* (2006.01)
(Continued)

(52) U.S. Cl.
CPC ..... *G01N 27/4062* (2013.01); *G01N 27/4067* (2013.01); *G01N 27/4077* (2013.01);
(Continued)

(58) Field of Classification Search
CPC ........... G01N 27/4062; G01N 27/4067; G01N 27/4077; H01R 43/20; H01R 13/42; H01R 4/4809; H01R 33/7685; Y02A 50/245
See application file for complete search history.

(56) References Cited

U.S. PATENT DOCUMENTS 7,568,378 B2 * 8/2009 Yoshikawa ........ G01N 27/4071
73/31.05
2009/0223818 A1 * 9/2009 Matsui ............... G01N 27/4062
204/412

(Continued)

FOREIGN PATENT DOCUMENTS

JP 2015-129727 A 7/2015

*Primary Examiner* — Louis J Rufo
(74) *Attorney, Agent, or Firm* — Leason Ellis LLP

(57) ABSTRACT

A gas sensor includes a sensing element having an electrode pad a metal terminal, and a separator that has insertion holes in which the metal terminal is held. The metal terminal includes a main body and an elastic portion that is integrally connected to the main body and is elastically connected to the electrode pad at a predetermined contact point. The main body includes a front-end-side restricting portion and a rear-end-side restricting portion that restrict the movement of the main body by contacting wall surfaces of the insertion hole when the main body moves in a direction intersecting the direction of an axial line. The contact point is located between the front-end-side restricting portion and the rear-end-side restricting portion in the direction of the axial line. The front-end-side restricting portion and the rear-end-side restricting portion are connected to each other so that a flat board portion is interposed therebetween.

9 Claims, 17 Drawing Sheets

(51) Int. Cl.
*H01R 13/42* (2006.01)
*G01N 27/407* (2006.01)
*G01N 33/00* (2006.01)
*H01R 4/48* (2006.01)
*H01R 33/76* (2006.01)

(52) U.S. Cl.
CPC ....... *G01N 33/0037* (2013.01); *H01R 4/4809* (2013.01); *H01R 13/42* (2013.01); *H01R 43/20* (2013.01); *H01R 33/7685* (2013.01); *Y02A 50/20* (2018.01)

(56) References Cited

U.S. PATENT DOCUMENTS

2014/0298931 A1* 10/2014 Oba .................. G01N 27/4062
73/866.5
2014/0299469 A1 10/2014 Oba et al.

* cited by examiner

FIG. 5A
FIG. 5B
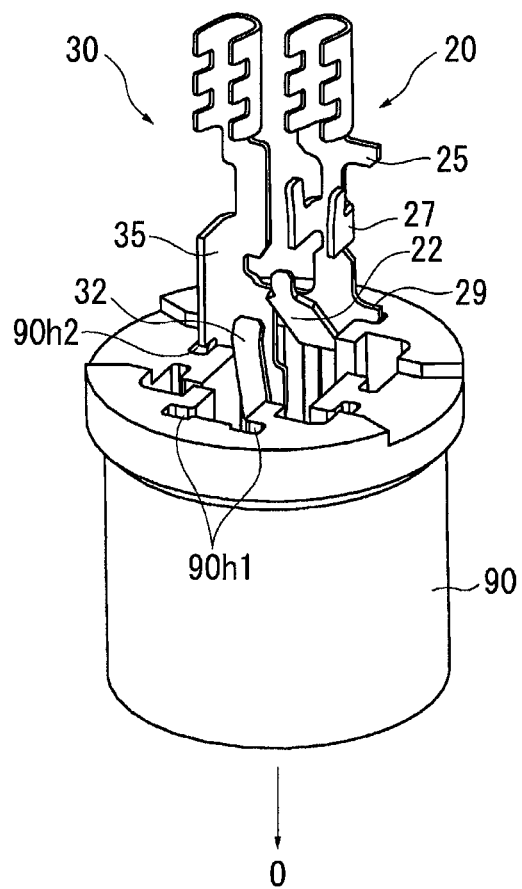
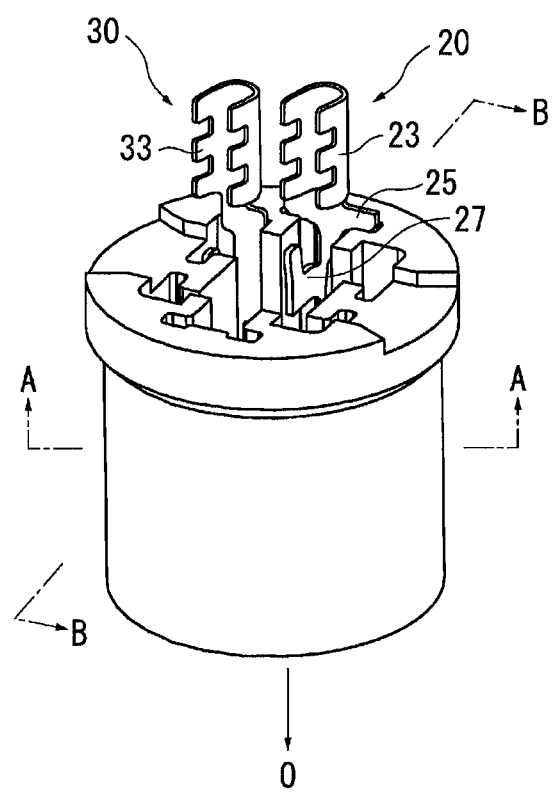

FIG. 16
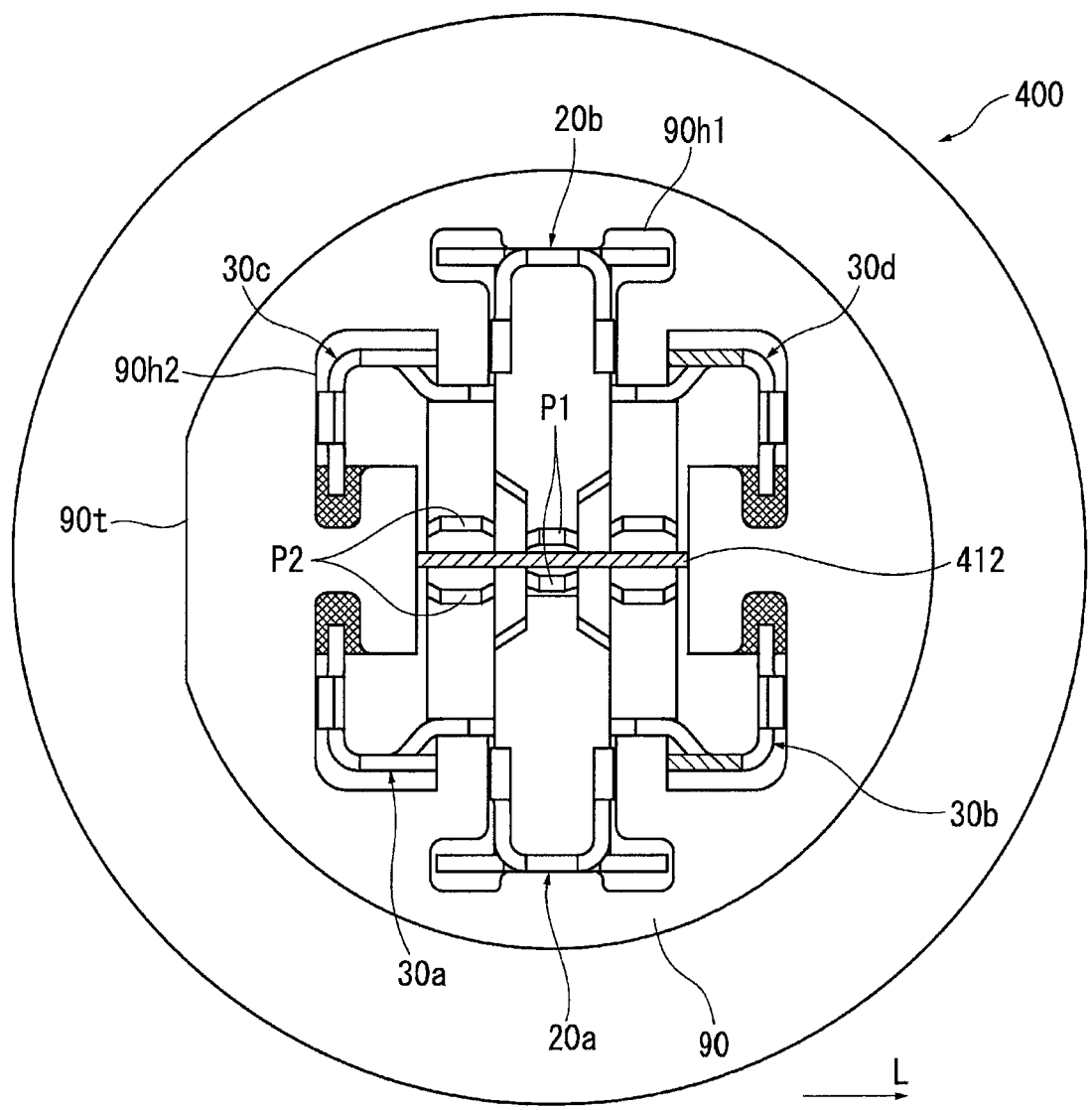
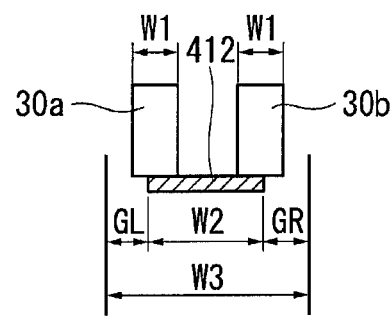

GAS SENSOR AND METHOD FOR MANUFACTURING THE SAME

This application claims the benefit of Japanese Patent Applications No. 2016-135101, filed Jul. 7, 2016 and No. 2017-128371, filed Jun. 30, 2017, both of which are incorporated herein by reference in their entireties.

FIELD OF THE INVENTION

The present invention relates to a gas sensor including a sensing element that detects the concentration of a gas to be detected and a method for manufacturing the gas sensor.

BACKGROUND OF THE INVENTION

A known gas sensor that detects the concentration of oxygen or NOx in an exhaust gas of, for example, an automobile includes a plate-shaped sensing element that uses a solid electrolyte.

This type of gas sensor, which is widely used, includes electrode pads disposed on a rear-end-side outer surface of the plate-shaped sensing element, metal terminals are in electrical contact with the respective electrode pads to output a sensor output signal from the sensing element to the outside, and power is supplied to a heater stacked on the sensing element (Japanese Unexamined Patent Application Publication No. 2015-129727 (FIG. 5)).

As illustrated in FIG. 19, a metal terminal 200 includes a main body 201 having a U-shaped section formed of strips, for example, in a manner in which a metallic plate is cut and raised, a folded portion 202 that is formed in a manner in which a part of the main body 201 on a front-end side is folded toward the sensing element (not illustrated) and that is elastically connected to one of the electrode pads of the sensing element, and a crimping portion 204 for crimping an end of a lead wire.

A pair of first positioning portions 206 are bent at 90 degrees and protrudes from both sides of a main surface (back surface) 200a of the main body 201 in the width direction. A pair of second positioning portions 208 extend from the front-end side of the main body 201 to both sides in the width direction.

When the metal terminal 200 is inserted into an insertion hole 1300h of a separator 1300, ends of the second positioning portions 208 come into contact with stepped portions 1300p on the front-end side of the insertion hole 1300h, and the metal terminal 200 is held in the insertion hole 1300h.

Technical Problem

As illustrated in FIG. 20, a clearance G is left between the metal terminal 200 and the insertion hole 1300h to smoothly insert the metal terminal 200 into the insertion hole 1300h of the separator 1300.

When the folded portion 202 comes into contact with an electrode pad 11a of a sensing element 10 at a contact point P, a reaction force F is applied from the electrode pad 11a to the outside (right-hand side in FIG. 20 or the side opposite the sensing element 10) in a radial direction.

At this time, a wall surface 1300h1 of the insertion hole 1300h to which the reaction force F is applied is in contact with only the back surface 208a of each second positioning portion 208 at a position nearer than the contact point P to the front-end side, and accordingly, moment acts in the direction of an arrow H such that the metal terminal 200 on the rear-end side moves toward the side (right-hand side in FIG. 20) opposite the sensing element 10 with the back surface 208a serving as a fulcrum. Consequently, there is a risk that the metal terminal 200 shifts from an axial line, and that the electrical connection between the electrode pad 11a and the metal terminal 200 becomes unstable. For example, when a vehicle equipped with the gas sensor vibrates during driving, moment also acts in the direction of the arrow H, and there is a risk that the metal terminal 200 shifts from the axial line, and that the electrical connection becomes unstable.

In view of this, an object of the present invention is to provide a gas sensor that enables the metal terminal to be held inside the separator with certainty and that enables the electrode pad of the sensing element and the metal terminal to be electrically connected to each other in a stable manner, and a method for manufacturing the gas sensor.

SUMMARY OF THE INVENTION

Solution to Problem

To solve the above problems, a gas sensor according to the present invention includes a sensing element that is formed in a plate shape extending in a direction of an axial line and that includes an electrode pad on an outer surface of a rear-end side of the sensing element, a metal terminal that extends in the direction of the axial line and that is electrically connected to the electrode pad, and a tubular separator that has an insertion hole in which the metal terminal is held and that surrounds a part of the sensing element on the rear-end side. The metal terminal includes a main body and an elastic portion that is integrally connected to the main body, said elastic portion being folded toward the sensing element and elastically connected to the electrode pad at a predetermined contact point. The main body includes a front-end-side restricting portion and a rear-end-side restricting portion both of which restrict a movement of the main body by contacting a wall surface of the insertion hole when the main body moves in a direction intersecting the direction of the axial line. The contact point is located between the front-end-side restricting portion and the rear-end-side restricting portion in the direction of the axial line. The front-end-side restricting portion and the rear-end-side restricting portion are connected to each other in a state where a flat board portion forming a part of the metal terminal is interposed therebetween.

When the elastic portion of the metal terminal comes into contact with the electrode pad of the sensing element at the contact point, a reaction force is applied from the electrode pad, and the metal terminal slightly shifts from the axial line and is pressed toward the opposite side.

At this time, in this gas sensor, the front-end-side restricting portion and the rear-end-side restricting portion disposed so as to interpose the contact point in the direction of the axial line come into contact with the wall surface forming the insertion hole, and the metal terminal is supported. That is, further movement (shift) of the metal terminal in the direction intersecting the direction of the axial line inside the insertion hole is restricted by the front-end-side restricting portion and the rear-end-side restricting portion that interpose the contact point in the direction of the axial line. Thus, the metal terminal is inhibited from further shifting from the axial line about the contact point, and moment acting about the contact point of the metal terminal is smaller than that in the case where movement of the metal terminal is restricted at one location on the front-end side or the rear-end side of the contact point.

Consequently, the electrical connection between the electrode pad and the metal terminal can be inhibited from being unstable due to the shift of the metal terminal from the axial line. Similarly, when a vehicle equipped with the gas sensor vibrates during driving, the occurrence of moment about the contact point of the metal terminal is reduced, and the metal terminal can be inhibited from shifting from the axial line.

Since the front-end-side restricting portion and the rear-end-side restricting portion are connected to each other with the flat board portion interposed therebetween, the front-end-side restricting portion and the rear-end-side restricting portion can be accurately formed at expected positions without strain due to residual stress as in the case where the restricting portions are formed by a bending process, and the metal terminal can be inhibited from shifting from the axial line with more certainty.

Naturally, the "flat board" does not need flatness but permits slight irregularity.

In the gas sensor according to the present invention, a distance between a front end of the front-end-side restricting portion and a rear end of the rear-end-side restricting portion in the direction of the axial line may exceeds a half of a length of the metal terminal in the direction of the axial line inside the insertion hole.

In this gas sensor, a span (distance L2) in the direction of the axial line O when opposed surfaces restrict movement of the metal terminal in front and behind of the contact point increases against the length L1, and the occurrence of moment about the contact point of the metal terminal can be further reduced.

In the gas sensor according to the present invention, a burr on the main body that protrudes toward an elastic portion side from surfaces opposite to surfaces that face the wall surface of the separator forming the insertion hole.

This gas sensor inhibits the burr from protruding toward and interfering with the wall surface of the separator and enables the opposed surface to be in close contact with the wall surface, so that movement of the metal terminal in the direction intersecting the direction of the axial line can be restricted with certainty. In addition, it is not necessary for the burr to be removed, and productivity is improved. The burr is a "residue outside a geometric shape at an edge of a corner, and a residue on a component during machining or molding", which is defined in JIS-B0051 (2004).

A method according to a first aspect of the present invention for manufacturing the gas sensor is a method for manufacturing the above gas sensor. The sensing element includes one or more pairs of the electrode pads on a front surface and a back surface thereof. The metal terminals are held in the insertion hole of the separator such that the contact points face each other. The method includes a separator accommodating step of accommodating the separator from a rear-end side of a first jig and inserting a planar portion to a position corresponding to opposed surfaces in the insertion hole of the separator by using the first jig that has an accommodating space in which the separator is accommodated in the direction of the axial line and the planar portion having a predetermined thickness that is disposed at the position corresponding to the opposed surfaces of the contact points and that extends along a part of the separator on the rear-end side from a bottom surface of the accommodating space when the separator and the metal terminals are accommodated in the accommodating space, a metal-terminal holding step of inserting the metal terminals into the insertion hole from a rear-end side of the separator and holding the metal terminals such that the planar portion is interposed between the contact points, and a jig removing step of relatively removing the first jig from the separator to a front-end side.

In the method according to the first aspect for manufacturing the gas sensor, when one or more pairs of the metal terminals are installed in the separator such that the contact points face each other, the planar portion of the first jig is interposed between the contact points. Accordingly, the metal terminals that face each other are inhibited from coming into contact and being entangled with each other, the metal terminals are inhibited from being damaged and deformed, and workability can be improved.

A method according to a second aspect of the present invention for manufacturing the gas sensor is a method for manufacturing the above gas sensor. The sensing element includes one or more pairs of the electrode pads on a front surface and a back surface thereof. The metal terminals are held in the insertion hole of the separator such that the contact points face each other. The method includes a lead-wire inserting step of inserting lead wires to be connected to the respective metal terminals into the insertion hole of the separator such that the lead wires protrude from a front-end side of the insertion hole, a metal-terminal connecting step of electrically connecting the metal terminals to ends of the lead wires, a metal-terminal accommodating step of accommodating the metal terminals from a rear-end side of a second jig such that a planar portion is interposed between the contact points by using the second jig that has an accommodating space whose inner diameter is equal to or smaller than a maximum outer diameter of an end portion of the separator and in which the metal terminals are accommodated in the direction of the axial line at the same positions as positions of the metal terminals to be held in the separator and the planar portion having a predetermined thickness that is disposed at a position corresponding to opposed surfaces of the contact points and that extends in the direction of the axial line from a bottom surface of the accommodating space when the metal terminals are accommodated in the accommodating space, a separator contacting step of bringing an end of the separator into contact with a rear end of the second jig while pulling the lead wires toward the rear-end side, a metal-terminal holding step of inserting the metal terminals into the insertion hole from the front-end side of the insertion hole of the separator in contact with the rear end of the second jig to hold the metal terminals, and a jig removing step of relatively removing the second jig from the separator to a front-end side.

In the method according to the second aspect for manufacturing the gas sensor, when one or more pairs of the metal terminals are installed in the separator such that the contact points face each other, the planar portion of the second jig is interposed between the contact points. Accordingly, the metal terminals that face each other are inhibited from coming into contact and being entangled with each other, the metal terminals are inhibited from being damaged and deformed, and workability can be improved.

Advantageous Effects of Invention

The present invention can obtain a gas sensor that enables the metal terminal to be held inside the separator with certainty and that enables the electrode pad of the sensing element and the metal terminal to be electrically connected to each other in a stable manner.

BRIEF DESCRIPTION OF THE DRAWINGS

These and other features and advantages of the present invention will become more readily appreciated when considered in connection with the following detailed description and appended drawings, wherein like designations denote like elements in the various views, and wherein:

FIGS. 5A and 5B are process drawings in which one of the metal terminals is being inserted into a corresponding one of insertion holes of the front-end-side separator.

FIG. 16 illustrates a state where the metal terminals are accommodated in the second jig.

DETAILED DESCRIPTION OF THE INVENTION

Embodiments of the present invention will hereinafter be described.

Figure 1:
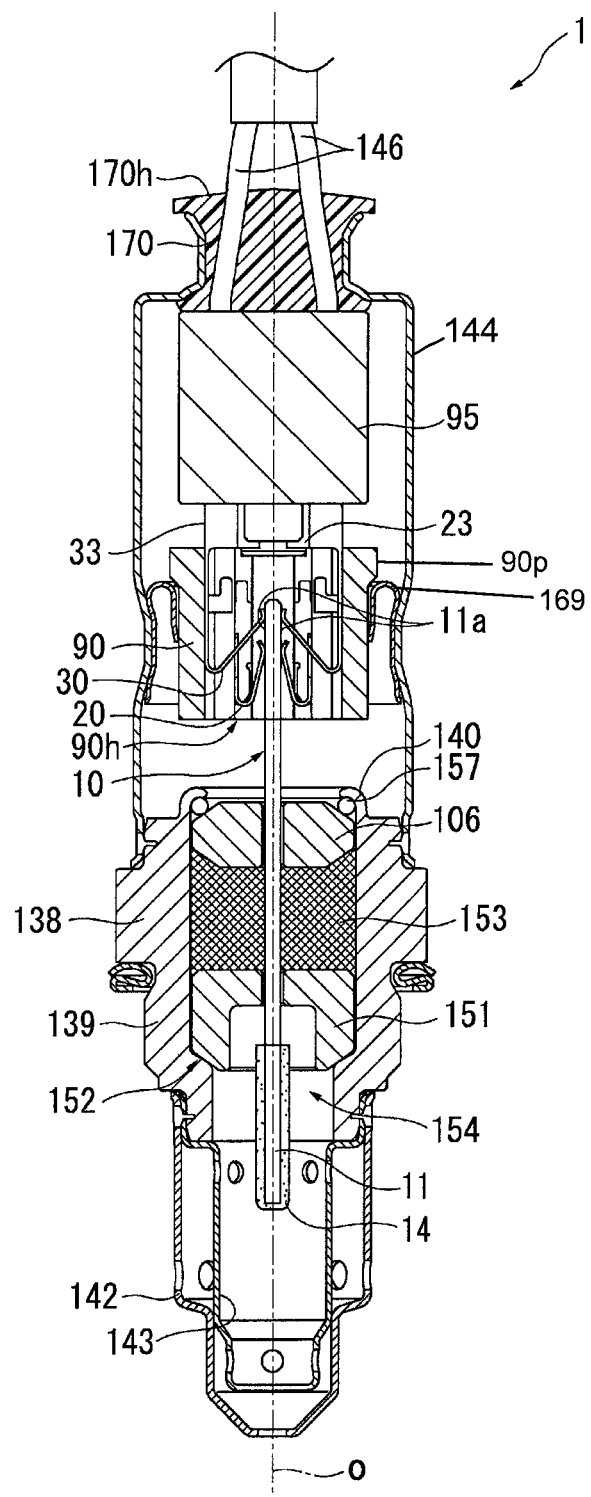
FIG. 1 is a sectional view of a gas sensor according to an embodiment of the present invention in a direction of an axial line.
Figure 2:
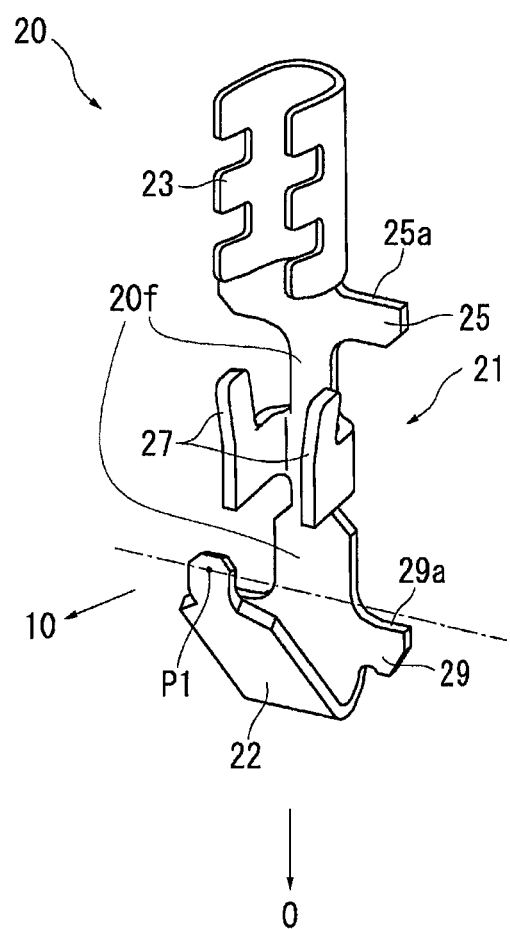
FIG. 2 is a perspective view of a metal terminal.
Figure 3:
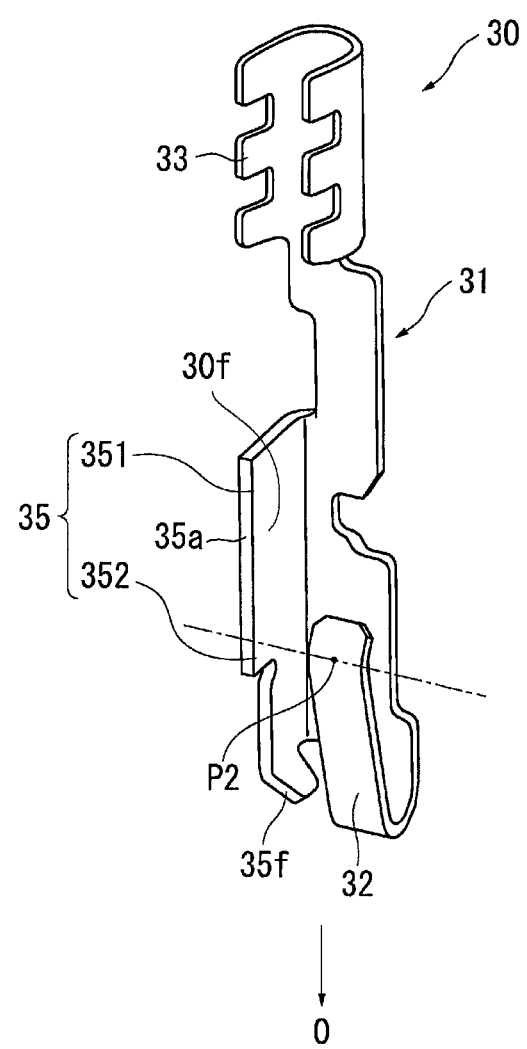
FIG. 3 is a perspective view of another metal terminal.
Figure 4:
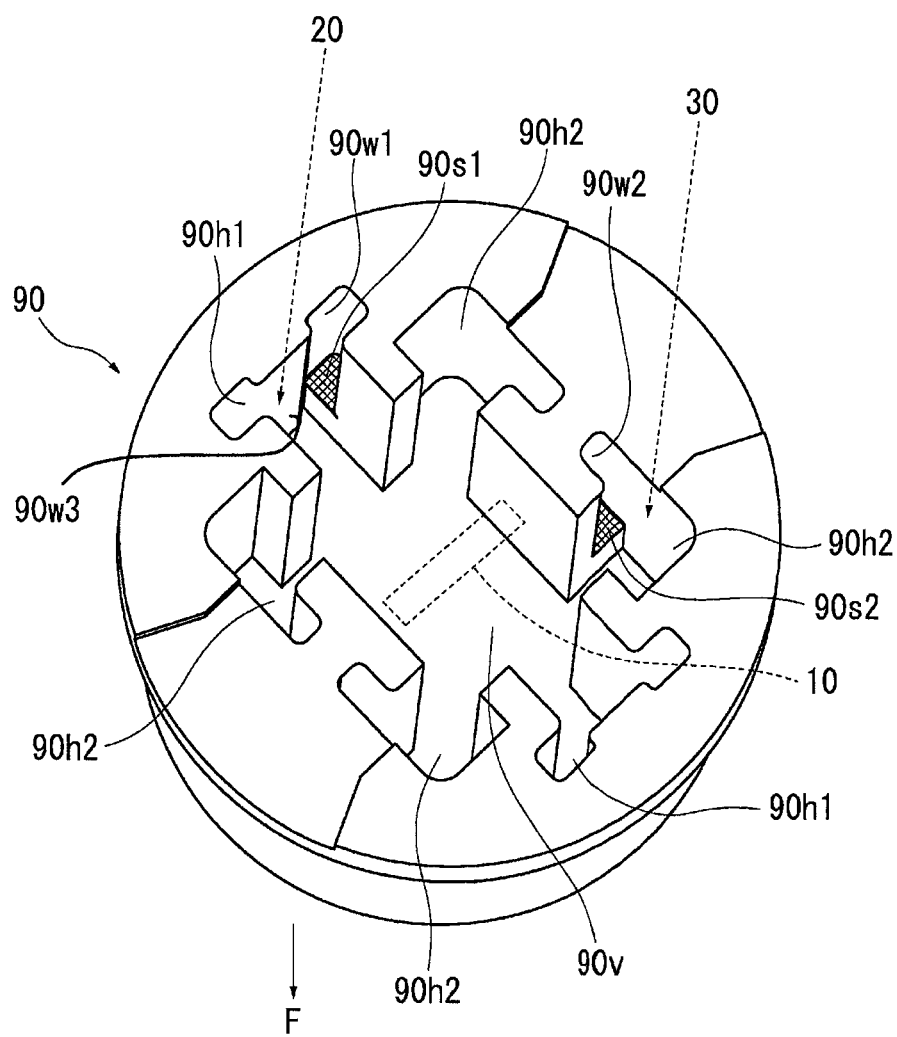
FIG. 4 is a perspective view of a front-end-side separator.
Figure 6:
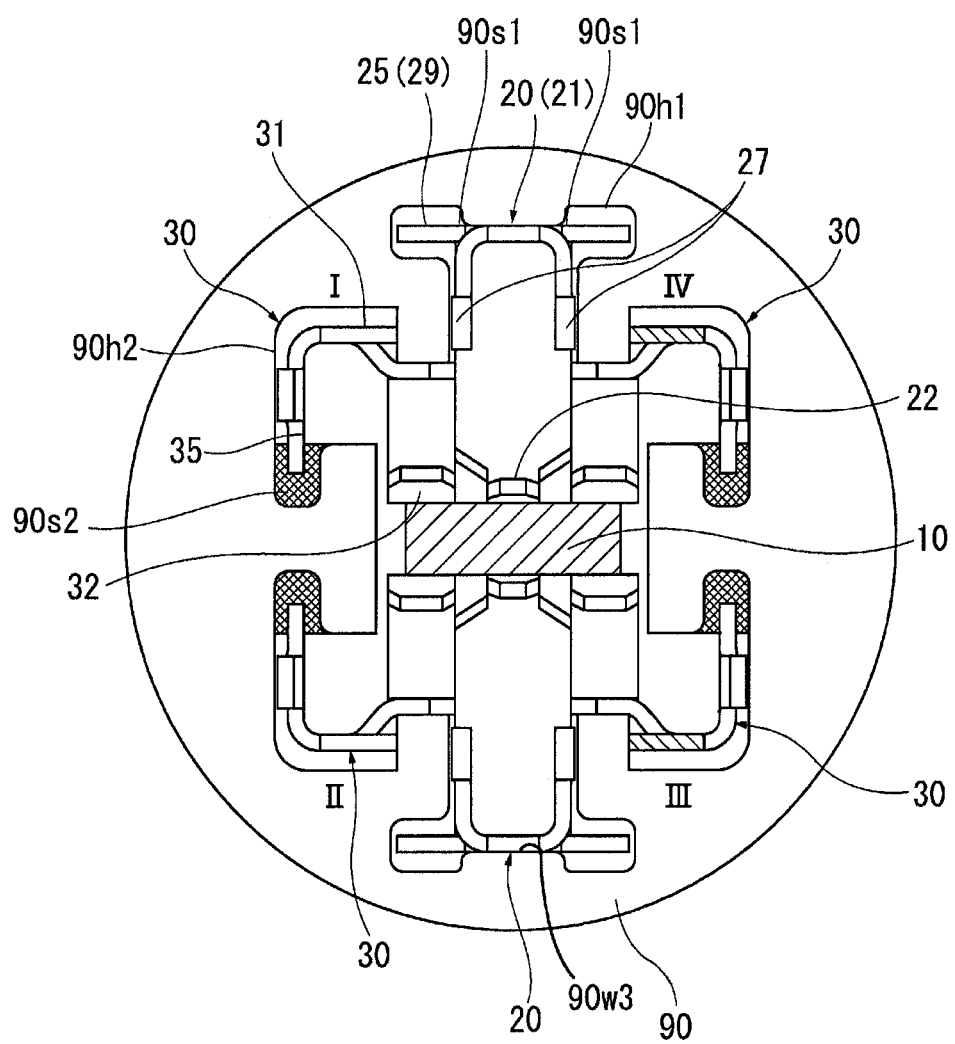
FIG. 6 is a sectional diagram in a radial direction illustrating a state where the metal terminals are held by the front-end-side separator.
Figure 7:
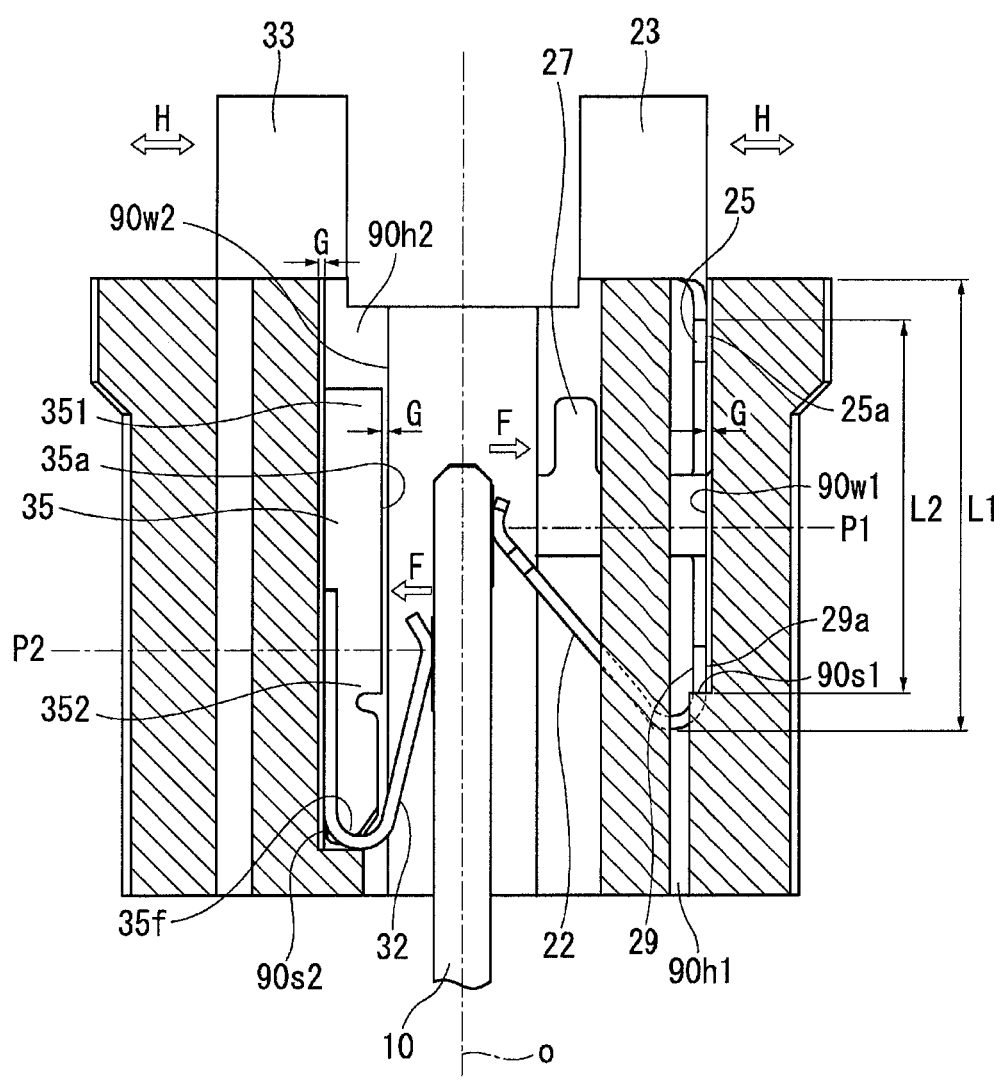
FIG. 7 is a sectional diagram in the direction of the axial line illustrating a state where the metal terminals are inserted and held in the insertion holes of the front-end-side separator.

FIG. 1 is a full sectional view of a gas sensor (NOx sensor) 1 according to an embodiment of the present invention in the direction of an axial line O. FIG. 2 and FIG. 3 are perspective views of metal terminals 20 and 30. FIG. 4 is a perspective view of a front-end-side separator 90. FIGS. 5A and 5B are process drawings in which one of the metal terminals 20 is being inserted into a corresponding one of insertion holes 90h of the front-end-side separator 90. FIG. 6 is a sectional diagram in the radial direction illustrating a state where the metal terminals 20 are inserted and held in the insertion hole 90h of the front-end-side separator 90. FIG. 7 is a sectional diagram in the direction of the axial line O illustrating a state where the metal terminals 20 are inserted and held in the insertion holes 90h of the front-end-side separator 90. FIG. 6 illustrates a section that is along line A-A in FIG. 5B and that is perpendicular to the direction of the axial line O. FIG. 7 illustrates a section that is along line B-B in FIG. 5B and that is along the direction of the axial line O.

The gas sensor 1 is a NOx sensor that detects oxygen concentration in an exhaust gas of an automobile or various internal combustion engines.

In FIG. 1, the gas sensor 1 includes a tubular metal shell 138 including a screw portion 139 used to be secured to an exhaust pipe and formed on an outer surface, a plate-shaped sensing element 10 extending in the direction of the axial line O (the longitudinal direction of the gas sensor 1 or the vertical direction in the figure), a tubular ceramic sleeve 106 disposed such that the ceramic sleeve 106 surrounds the sensing element 10 in the radial direction, the front-end-side separator 90 that is formed of a ceramic tube and that is disposed in an interior space on the front-end side thereof such that the front-end-side separator 90 surrounds a rear-end portion of the sensing element 10, and six metal terminals 20 and 30 (only four metal terminals are illustrated in FIG. 1) that are inserted and held in the insertion holes 90h extending through the front-end-side separator 90 in the direction of the axial line O.

A rear-end-side separator 95 that is formed of a ceramic tube is disposed on and in contact with the front-end-side separator 90 on the rear-end side, as described later.

The front-end-side separator 90 corresponds to a "separator" in CLAIMS.

The six insertion holes 90h of the front-end-side separator 90 are in communication with the interior space on the front-end side of the front-end-side separator 90. The metal terminals 20 and 30 face the outer surface of the sensing element 10 on the rear-end side and are electrically connected to electrode pads 11a to 12c (see FIG. 9) formed on the outer surface.

Three of the electrode pads 11a to 12c are arranged in the width direction on both surfaces of the sensing element 10 on the rear-end side. The electrode pads 11a to 12c can be formed, for example, as sintered bodies mainly formed of Pt.

A gas-detecting portion 11 at an end of the sensing element 10 is coated with a porous protective coat 14 such as alumina.

Figure 9:
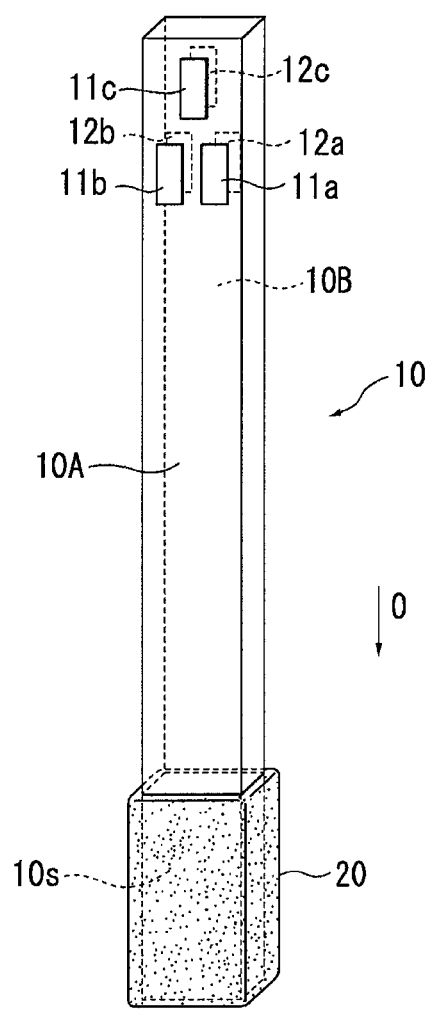
FIG. 9 is a perspective view of a sensing element.

As illustrated in FIG. 9, the sensing element 10 is formed in a plate shape extending in the direction of the axial line O and formed of a gas-detecting portion 11 whose end portion 10s detects oxygen concentration and NOx concentration. The gas-detecting portion 11 is coated with the porous protective coat 14. The sensing element 10 itself has a known structure and includes the gas-detecting portion including a NOx detecting cell, a reference cell, and an oxygen concentration cell having a solid electrolyte body permeable to oxygen ions and a pair of electrodes, and a heater that heats the gas-detecting portion and that maintains a constant temperature thereof, although this is not illustrated.

The two electrode pads 11a and 11b are arranged in the direction of the width W on the rear-end side of a main surface (front surface) 10A of the sensing element 10. A sensor output signal from the oxygen concentration cell is outputted from the electrode pads 11a and 11b via a lead portion (not illustrated). The electrode pad 11c is formed between the electrode pads 11a and 11b in the width direction at a position nearer than the electrode pads 11a and 11b to the front-end side in the direction of the axial line O.

The two electrode pads 12a and 12b are arranged in the width direction on the rear-end side of the other main surface (back surface) 10B that faces the main surface 10A. Power is supplied to the heater via the lead portion (not illustrated). The electrode pad 12c is formed between the electrode pads 12a and 12b in the width direction at a position nearer than the electrode pads 12a and 12b to the front-end side in the direction of the axial line O.

The electrode pad 11c applies a reference voltage to the reference cell via the lead portion. A sensor output signal from the NOx cell is outputted from the electrode pad 12c via the lead portion.

The electrode pads 11a to 12c are rectangular and elongated in the direction of the axial line O and can be formed as, for example, sintered bodies mainly formed of Pt. According to the present embodiment, the electrode pads 11a, 11b, and 11c and the electrode pads 12a, 12b, and 12c, which are disposed on the surfaces of the sensing element 10, respectively face and are paired with each other with the sensing element 10 interposed therebetween. Specifically, a pair of the electrode pad 11a and the electrode pad 12a face each other, another pair of the electrode pad 11b and the electrode pad 12b face each other, and the other pair of the electrode pad 11c and the electrode pad 12c face each other. In other words, according to the present embodiment, there are three pairs of the electrode pads 11a to 12c.

The six metal terminals 20 and 30 are held in the insertion holes 90h (90h1 and 90h2) of the separator 90 (FIG. 4). The two metal terminals 20 that face the electrode pads 11c and 12c with the sensing element 10 interposed therebetween and the four metal terminals 30 that face the electrode pads 11a, 12a, 11b, and 12b with the sensing element 10 interposed therebetween correspond to "pairs of the metal terminals" (see FIG. 4). In other words, according to the present embodiment, there are three pairs of the metal terminals 20 and 30.

The metal shell 138 is composed of stainless steel, has a through-hole 154 extending in the direction of the axial line, and is formed in a substantially tubular shape having a ledge 152 protruding toward the inside of the through-hole 154 in the radial direction. The sensing element 10 is disposed in the through-hole 154 such that an end portion of the sensing element 10 protrudes from an end thereof. The ledge 152 is formed so as to have a tapered surface inclined inward with respect to a plane perpendicular to the direction of the axial line.

Inside the through-hole 154 of the metal shell 138, an alumina ceramic holder 151 having a substantially annular shape, a powder-filled layer 153 (also referred to below as a talc ring 153), and the ceramic sleeve 106 are stacked in this order from the front-end side to the rear-end side in a state where the sensing element 10 is surrounded in the radial direction.

A sheet packing 157 is disposed between the ceramic sleeve 106 and a rear-end portion 140 of the metal shell 138. The rear-end portion 140 of the metal shell 138 is crimped so as to press the ceramic sleeve 106 toward the front-end side with the sheet packing 157 interposed therebetween.

As illustrated in FIG. 1, an outer protector 142 and an inner protector 143, as a metallic (for example, stainless steel) double protector, which cover the protruding portion of the sensing element 10 and have holes, are installed on the outer circumference of the metal shell 138 on the front-end side (lower side in FIG. 1) by, for example, welding.

A metal pipe 144 is secured to the outer circumference of the metal shell 138 on the rear-end side. A rubber grommet 170, which has a lead-wire insertion hole 170h in which four lead wires 146 (only two lead wires are illustrated in FIG. 1) electrically connected to the six metal terminals 20 and 30 (only four metal terminals are illustrated in FIG. 1) of the sensing element 10 are inserted, is disposed in an opening of the metal pipe 144 on the rear-end side (upper side in FIG. 1).

The lead wires 146 are pulled from the rear-end side of the metal terminals 20 and 30 toward the rear-end side of the front-end-side separator 90, extend through an insertion hole (not illustrated) of the rear-end-side separator 95 and the grommet 170, and are pulled to the outside of the gas sensor 1.

The front-end-side separator 90 is disposed on the rear-end side (upper side in FIG. 1) of the sensing element 10 protruding from the rear-end portion 140 of the metal shell 138, and a flange portion 90p protruding from an outer surface outward in the radial direction is provided. The front-end-side separator 90 is held inside the metal pipe 144 in a manner in which the flange portion 90p is in contact with the metal pipe 144 with a holding member 169 interposed therebetween.

The rear-end-side separator 95 is disposed between the grommet 170 and the front-end-side separator 90. The rear-end-side separator 95 presses the front-end-side separator 90 toward the front-end side by using an elastic force of the grommet 170. Thus, the flange portion 90p is pressed against the holding member 169, and the front-end-side separator 90 and the rear-end-side separator 95 are held inside the metal pipe 144.

FIG. 2 and FIG. 3 are perspective views of the metal terminals 20 and 30, respectively. According to the present embodiment, two kinds of the metal terminals 20 and 30 are used.

As illustrated in FIG. 6, regarding the four front-end-side metal terminals 30, the front-end-side metal terminals 30 adjacent to each other in the front-end-side separator 90 are symmetric with each other with respect to a line, and accordingly, one of the front-end-side metal terminals 30 (at a position I on the upper left side in FIG. 6) is described.

The front-end-side metal terminal 30 on the lower left side at a position II in FIG. 6 is symmetric with the front-end-side metal terminal 30 at the position I with respect to a line extending in the direction along a surface of the sensing element 10. The front-end-side metal terminal 30 on the lower right side at a position III in FIG. 6 is symmetric with the front-end-side metal terminal 30 at the position II with respect to a line perpendicular to the direction along a surface of the sensing element 10. The front-end-side metal terminal 30 on the upper right side at a position IV in FIG. 6 is symmetric with the front-end-side metal terminal 30 at the position I with respect to the line perpendicular to the direction along a surface of the sensing element 10.

Regarding the two front-end-side metal terminals 20, the front-end-side metal terminals 20 adjacent to each other in the front-end-side separator 90 are symmetric with each other with respect to a line, and accordingly, one of the front-end-side metal terminals 20 (at an upper position in FIG. 6) is described.

The front-end-side metal terminal 20 on the lower side in FIG. 6 is symmetric with the front-end-side metal terminal 20 on the upper side with respect to a line extending the direction along a surface of the sensing element 10. Each front-end side metal terminal 20 is located between the front-end-side metal terminals 30 in the width direction of the sensing element 10.

As illustrated in FIG. 2, each of the metal terminals 20 extends in the direction of the axial line O as a whole and includes a lead-wire-connecting portion 23 that is connected to the corresponding lead wire 146 (see FIG. 1), a substantially plate-shaped main body 21 connected to the lead-wire-connecting portion 23 on the front-end side, and an elastic portion 22 that is folded toward the sensing element 10 on the front-end side of the main body 21, which are integrally formed. A flat surface of the main body 21 forms a flat board portion 20f.

The metal terminals 20 can be manufactured, for example, in a manner in which a metallic plate (Inconel (registered trademark), for example) is punched and subsequently folded into a predetermined shape, but are not limited thereto.

The lead-wire-connecting portion 23 is a known tubular press-fit terminal. A part of the lead wire 146 at which a covering is removed and a conducting wire is exposed is inserted into the tube and press-fitted, so that the lead wire 146 is electrically connected thereto.

Outer portions of the main body 21 on both sides in the width direction are folded at 90 degrees toward the sensing element 10 at the center in the direction of the axial line O and form holding portions 27 having a U-shaped section. The main body 21 serves as a base portion of each metal terminal 20 and maintains the strength of the metal terminal 20. The distance between the pair of the holding portions 27 gradually increases in the direction to the rear-end side.

A pair of rectangular rear-end-side restricting portions 25 that are flush with the main body 21 extend from both sides of the main body 21 in the width direction toward the outside on the rear-end side in the direction of the axial line O. Similarly, a pair of rectangular front-end-side restricting portions 29 that are flush with the main body 21 extend from both sides of the main body 21 in the width direction toward the outside on the front-end side in the direction of the axial line O.

The elastic portion 22 is folded from an end of the main body 21 toward the sensing element 10 and the rear-end side and is elastically connected to the electrode pad 11c or 12c (see FIG. 1 and FIG. 9) at a contact point P1. The elastic portion 22 elastically bends in the radial direction with respect to the main body 21.

The back surfaces (surfaces opposite the elastic portion 22) 29a and 25a of the front-end-side restricting portions 29 and the rear-end-side restricting portions 25 correspond to "opposed surfaces" that face the wall surface of the separator forming the insertion holes in CLAIMS.

As illustrated in FIG. 3, each of the metal terminals 30 extends in the direction of the axial line O as a whole and includes a lead-wire-connecting portion 33 that is connected to the corresponding lead wire 146 (see FIG. 1), a main body 31 connected to the lead-wire-connecting portion 23 on the front-end side, and an elastic portion 32 that is folded toward the sensing element 10 on the front-end side of the main body 31, which are integrally formed.

The metal terminals 30 can be manufactured, for example, in a manner in which a metallic plate (Inconel (registered trademark), for example) is punched and subsequently folded into a predetermined shape, but are not limited thereto.

Each lead-wire-connecting portion 33 is a press-fit terminal as in the case of the lead-wire-connecting portion 23. Each lead wire 146 is electrically connected thereto.

The main body 31 has an L-shaped section, and an outer portion thereof in the width direction is folded at 90 degrees toward the sensing element 10 and forms a position-restricting portion 35. A flat surface of the position-restricting portion 35 forms a flat board portion 30f. The main body 31 serves as a base portion of each metal terminal 30 and maintains the strength of the metal terminals 30.

The elastic portion 32 is folded from an end of the main body 31 toward the sensing element 10 and the rear-end side and is elastically connected to the electrode pad 11a, 12a, 11b, or 12b (see FIG. 9) at a contact point P2. The elastic portion 32 elastically bends in the radial direction with respect to the main body 31.

An end portion 35f of the position-restricting portion 35 is folded in the width direction of the main body 31 inward (toward the elastic portion 32). A part of the position-restricting portion 35 nearer than the contact point P2 to the front-end side forms a front-end-side restricting portion 352 and a part thereof nearer than the contact point P2 to the rear-end side forms a rear-end-side restricting portion 351, which is described in detail later.

An edge surface (surface on the same side of the elastic portion 32) 35a of the position-restricting portion 35 corresponds to one of the "opposed surfaces" that face the wall surface of the separator forming the insertion holes in CLAIMS.

As illustrated in FIG. 4, the front-end-side separator 90 has the insertion holes 90h (90h1 and 90h2). The insertion holes 90h1 and 90h2 are in communication with an interior space 90v on the side of an end F of the front-end-side separator 90.

The insertion holes 90h2 are located at four corners of the front-end-side separator 90. The insertion holes 90h1 are located between the insertion holes 90h2 in the width direction of the sensing element 10.

A rear-end facing surface 90s1 is formed on the front-end side of each insertion hole 90h1. A rear-end facing surface 90s2 is formed on the front-end side of each insertion hole 90h2.

As illustrated in FIGS. 5A and 5B, when each metal terminal 20 is inserted into the corresponding insertion hole 90h1 of the front-end-side separator 90, the front-end-side restricting portions 29 and the rear-end-side restricting portions 25 are inserted toward the front-end side along a groove of the insertion hole 90h1, and an end of one of the front-end-side restricting portions 29 comes into contact with the rear-end facing surface 90s1 of the insertion hole 90h1 on the front-end side, and the position thereof in the direction of the axial line O is set. The pair of the holding portions 27 that have a gradually increased distance from each other in the direction to the rear-end side are in contact with the wall surface of the insertion hole 90h1, and the metal terminal 20 is held in the insertion hole 90h1.

Similarly, when each metal terminal 30 is inserted into the corresponding insertion hole 90h2 of the front-end-side separator 90, the position-restricting portion 35 is inserted toward the front-end side along a substantially L-shaped groove of the insertion hole 90h2, and an end 35f of the position-restricting portion 35 comes into contact with the rear-end facing surface 90s2 of the insertion hole 90h2, and the position thereof in the direction of the axial line O is set.

As illustrated in FIGS. 5A and 5B, the insertion holes 90h2 are located at four corners of the front-end-side separator 90. The insertion holes 90h1 are located between the insertion holes 90h2 in the width direction of the sensing element 10.

As illustrated in FIG. 7, the front-end-side restricting portions 29 and the rear-end-side restricting portions 25 of each metal terminal 20 face a wall surface 90w1 (see FIG. 4) of the corresponding insertion hole 90h1 along the direction of the axial line O on the side opposite the sensing element 10 with a clearance G interposed therebetween. Specifically, the back surfaces 29a and 25a (see FIG. 2) of the front-end-side restricting portions 29 and the rear-end-side restricting portions 25 opposite the sensing element 10 face the wall surface 90w1.

Similarly, the position-restricting portion 35 of each metal terminal 30 faces a wall surface 90w2 (see FIG. 4) of the corresponding insertion hole 90h2 along the direction of the axial line O on the side of the sensing element 10 with the clearance G interposed therebetween. Specifically, the edge surface 35a (see FIG. 2) of the position-restricting portion 35 on the side of the sensing element 10 faces the wall surface 90w2.

In a view from the direction of the axial line O, the back surfaces 29a and 25a of the front-end-side restricting portions 29 and the rear-end-side restricting portions 25 overlap (are flush with each other). Similarly, in a view from the direction of the axial line O, the edge surface 35a of the position-restricting portion 35 is a straight line (parallel to the direction of the axial line O).

In FIG. 7, one of the metal terminals 20 and 30 that face each other is omitted for easy understanding.

When each elastic portion 22 comes into contact with the electrode pad 11c or 12c of the sensing element 10 at the contact point P1, a reaction force F is applied from the electrode pad 11c or 12c toward the outside (right-hand side in FIG. 7 or the side opposite the sensing element 10) in the radial direction. At this time, the metal terminals 20 slightly shift from the axial line O and are pressed toward the back-surface side (right-hand side in FIG. 7), the back surfaces 29a and 25a of the front-end-side restricting portions 29 and the rear-end-side restricting portions 25 come into contact with the wall surface 90w1, and the metal terminals 20 are supported.

That is, further movement (shift) of the metal terminals 20 in the direction (radial direction of the front-end-side separator 90) intersecting the direction of the axial line O inside the insertion holes 90h1 is restricted at the same locations (back surfaces 29a and 25a) interposing the contact point P1 in the direction of the axial line O. Thus, the metal terminals 20 are inhibited from further shifting from the axial line O about the contact point P1, and moment acting about the contact point P1 of the metal terminals 20 is smaller than that in the case where movement of the metal terminals 20 is restricted at one location on the front-end side or the rear-end side of the contact point P1.

Consequently, the electrical connection between the electrode pads 11c and 12c and the metal terminals 20 can be inhibited from being unstable due to the shift of the metal terminals 20 from the axial line O. Similarly, when a vehicle equipped with the gas sensor 1 vibrates during driving, the occurrence of moment about the contact point P1 of the metal terminals 20 is reduced, and the metal terminals 20 can be inhibited from shifting from the axial line O.

Since the front-end-side restricting portions 29 and the rear-end-side restricting portions 25 are connected to each other with the flat board portion 20f interposed therebetween, the front-end-side restricting portions 29 and the rear-end-side restricting portions 25 can be accurately formed at expected positions without strain due to residual stress as in the case where the restricting portions 29 and 25 are formed by a bending process, and the metal terminals 20 can be inhibited from shifting from the axial line O with more certainty.

Also in the case of the metal terminals 30, when each elastic portion 32 comes into contact with the electrode pad 11a, 12a, 11b, or 12b of the sensing element 10 at the contact point P2, a reaction force F is applied from the electrode pad 11a, 12a, 11b, or 12b toward the outside (left-hand side in FIG. 7 or the side opposite the sensing element 10) in the radial direction. At this time, the metal terminals 30 slightly shift from the axial line O and are pressed toward the back-surface side (left-hand side in FIG. 7), the edge surface 35a of the position-restricting portion 35 comes into contact with the wall surface 90w2, and the metal terminals 30 are supported.

That is, further movement (shift) of the metal terminals 30 in the direction (radial direction of the front-end-side separator 90) intersecting the direction of the axial line O inside the insertion holes 90h2 is restricted at the same locations (edge surface 35a) interposing the contact point P2 in the direction of the axial line O. Thus, the metal terminals 30 are also inhibited from further shifting from the axial line O about the contact point P2.

The position-restricting portion 35 (edge surface 35a) extends in the direction of the axial line O beyond the contact point P2. A part of the position-restricting portion 35 (edge surface 35a) nearer than the contact point P2 to the front-end side forms the front-end-side restricting portion 352, and a part thereof nearer than the contact point P2 to the rear-end side forms the rear-end-side restricting portion 351.

Since the front-end-side restricting portion 352 and the rear-end-side restricting portion 351 are connected to each other with the flat board portion 30f interposed therebetween, the front-end-side restricting portion 352 and the rear-end-side restricting portion 351 can be accurately formed at expected positions without strain due to residual stress as in the case where the restricting portions 352 and 351 are formed by a bending process, and the metal terminals 30 can be inhibited from shifting from the axial line O with more certainty.

According to the present embodiment, as illustrated in FIG. 7, a distance L2 between the front end of the front-end-side restricting portions 29 and the rear end of the rear-end-side restricting portions 25 in the direction of the axial line O exceeds L1/2 where L1 is the length of the metal terminals 20 in the direction of the axial line O inside the insertion holes 90h1.

When the distance L2 exceeds ½ of the length L1, a span (distance L2) in the direction of the axial line O when the back surfaces 29a and 25a restrict movement of the metal terminals 20 in front and behind of the contact point P1 increases against the length L1, and the occurrence of moment about the contact point P1 can be further reduced.

The same is true for the metal terminals 30.

Figure 8:
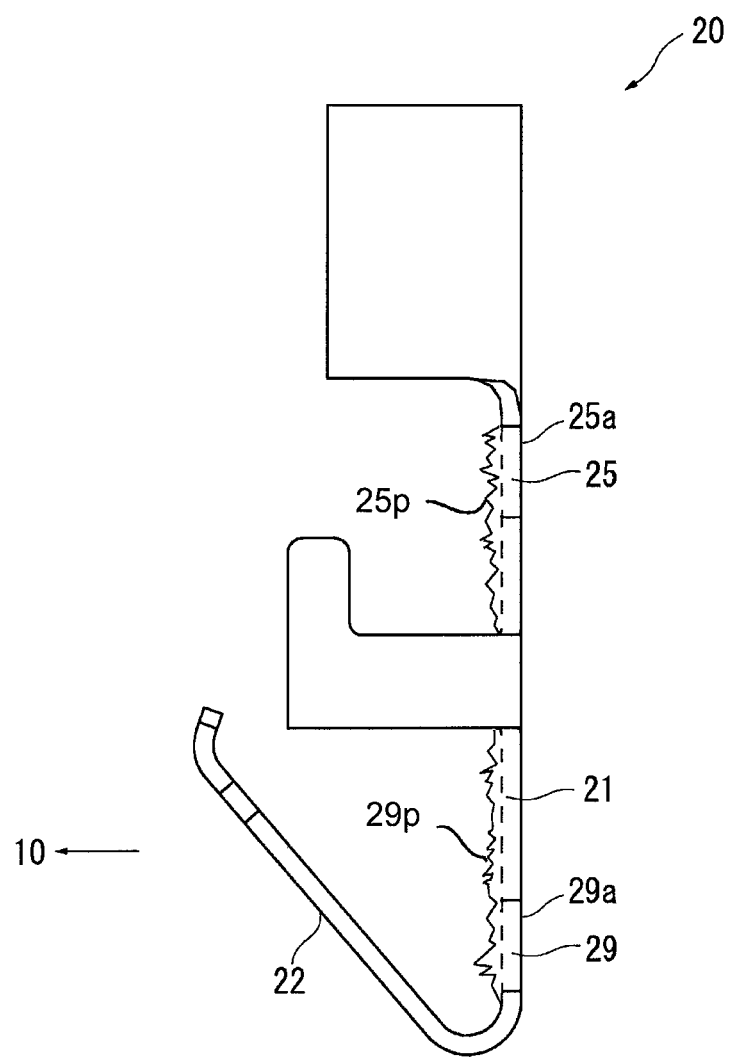
FIG. 8 is a side view of one of the metal terminals.

According to the present embodiment, as illustrated in FIG. 8, burrs 25P, 29P are formed on edge surfaces of the main body 21, the front-end-side restricting portions 29, and the rear-end-side restricting portions 25 so as to protrude toward the side of the elastic portion 22 (sensing element 10).

This inhibits the burrs from protruding from the back surfaces 29a and 25a toward the wall surfaces 90w1 and 90w3 and thereby interfering with the wall surfaces 90w1 and 90w3 (see FIG. 4 and FIG. 6). As a result, the back surfaces 29a and 25a can be in close contact with the wall surfaces 90w1 and 90w3, so that movement of the metal terminals 20 in the direction intersecting the direction of the axial line O can be restricted with certainty. In particular, when the burr protrudes toward the side of the back surfaces 29a and 25a facing the wall surface 90w3, there is a risk that the main body 21 is separated from the wall surface 90w3 in the opposite direction, the spring stroke of the elastic portion 22 increases, an excess load is applied to the sensing element 10, and the element is broken. Accordingly, it is more effective that the burr does not protrude thereto. In addition, it is not necessary to remove the burr. As a result, productivity is improved.

The burr is a "residue outside a geometric shape at an edge of a corner, and a residue on a component during machining or molding", which is defined in JIS-B0051 (2004). According to the present embodiment, burrs $29p$ and $25p$ are created, for example, when a metallic plate is punched with a press and sheared to manufacture the metal terminals 20.

A method according to a first aspect of an embodiment of the present invention for manufacturing the gas sensor will now be described with reference to FIG. 10 to FIGS. 13A-13D.

Figure 10:
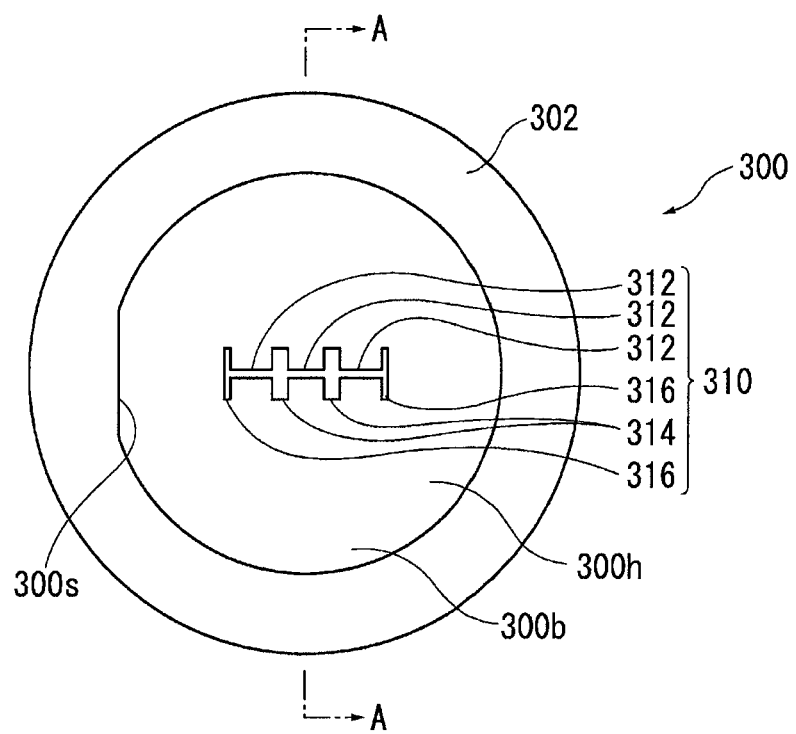
FIG. 10 is a plan view of a first jig used according to a first aspect of an embodiment.
Figure 11:
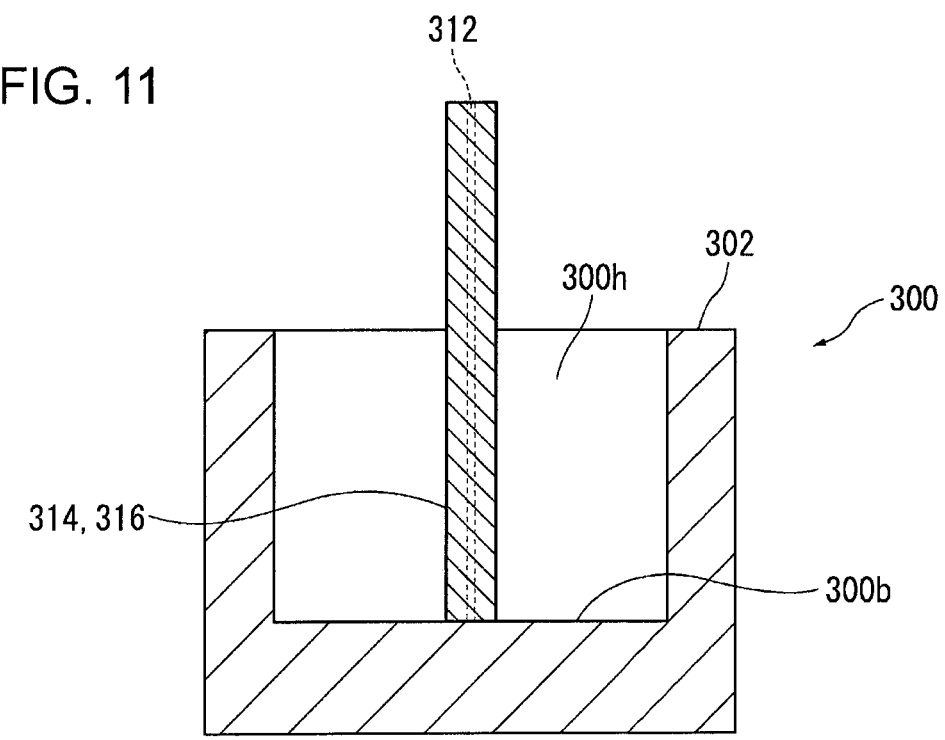
FIG. 11 is a sectional view of FIG. 10 taken along line A-A.
Figure 12:
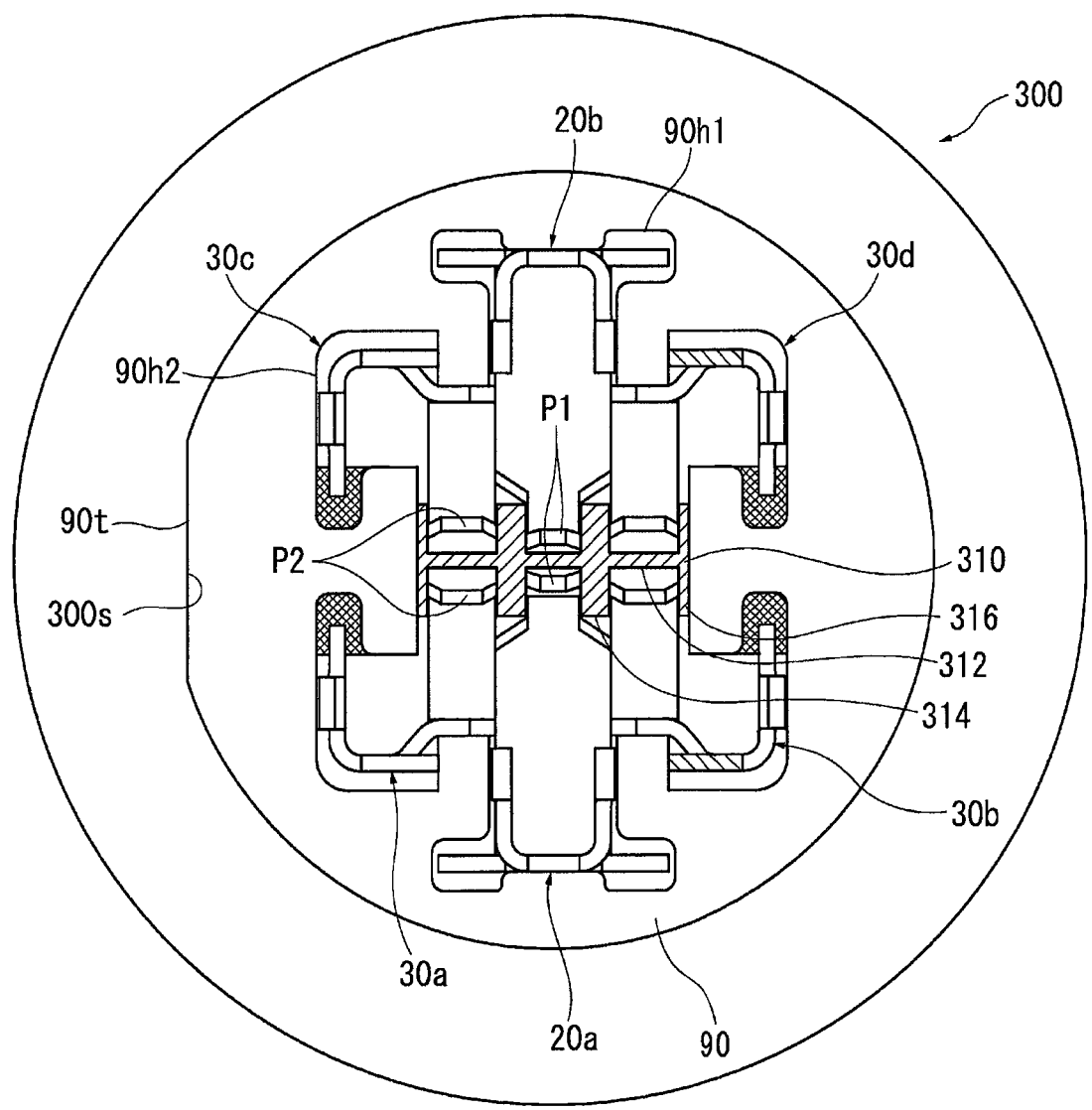
FIG. 12 illustrates a state where the metal terminals are inserted in the separator accommodated in the first jig.
Figure 13:
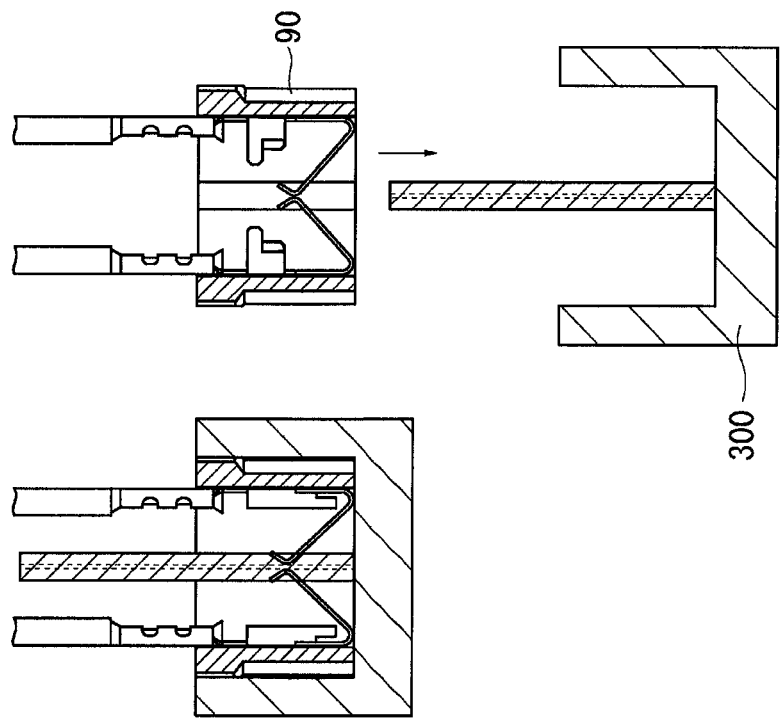
FIGS. 13A-13D are process drawings of a method according to the first aspect of the embodiment for manufacturing the gas sensor.

FIG. 10 is a plan view of a first jig 300 used according to the first aspect of the embodiment. FIG. 11 is a sectional view of FIG. 10 taken along line A-A. FIG. 12 illustrates a state where the metal terminals 20 and 30 are inserted in the separator (first separator) 90 accommodated in the first jig 300. FIGS. 13A-13D are process drawings of the method according to the first aspect of the embodiment for manufacturing the gas sensor.

As illustrated in FIG. 10 and FIG. 11, the first jig 300 is formed in a cylindrical shape with a bottom and has, at the center, a cylindrical accommodating space $300h$ that opens to the upper surface. A protruding portion 310 in the form of a substantially H-shape in a top view protrudes upward from the center of the bottom surface $300b$ of the accommodating space $300h$. The protruding portion 310 is formed at a position corresponding to the insertion hole $90h$ at the center of the separator 90.

The protruding portion 310 includes two prism portions 314 at the center, three planar portions 312 in a plate shape that connect the two prism portions 314 to each other, that extend from end portions of the two prism portions 314, and that are flush with each other, and two side wall portions 316 that vertically extend from both sides of the planar portions 312 and that each have ends flush with other opposed surfaces of the prism portions 314. The prism portions 314 and the side wall portions 316 protrude from flat surfaces of the planar portions 312. The three planar portions 312 are formed at positions corresponding to the opposed surfaces of a pair of metal terminals $20a$ and $20b$ at the contact points P1 and the opposed surfaces (see FIG. 12) of two pairs of metal terminals $30a$ to $30d$ at the contact points P2. The protruding portion 310 protrudes up to a position higher than the upper surface 302 of the first jig 300.

A portion around the accommodating space $300h$ forms a straight-line portion $300s$ and prevents rotation of the separator 90 in the circumferential direction, which is described later.

The first jig 300 and the protruding portion 310 can be made of, for example, metal such as stainless steel.

In a metal-terminal holding step of the method according to the first aspect of the embodiment for manufacturing the gas sensor, as illustrated in FIG. 12, the six metal terminals $20a$, $20b$, and $30a$ to $30d$ are inserted in six insertion holes $90h1$ and $90h2$ of the separator 90 accommodated in the first jig 300, which is described in detail later. At this time, the prism portions 314 and the side wall portions 316 come into contact with the side surfaces (surfaces intersecting surfaces of the elastic portions 22 and 32) of the metal terminals $20a$, $20b$, and $30a$ to $30d$ and restrict movement of the metal terminals in the width direction, and the metal terminals can be prevented from shifting inside the separator 90 (inside the first jig 300).

The detail of the method according to the first aspect of the embodiment for manufacturing the gas sensor will now be described with reference to FIGS. 13A-13D. FIGS. 13A-13D illustrate a pair of the metal terminals $30b$ and $30d$ only. However, the same is true for the other two pairs of the metal terminals, which are into the page and concealed in FIGS. 13A-13D.

The separator 90 is first moved from the rear-end side (upper side) of the first jig 300 in the direction of the axial line and accommodated, and the planar portions 312 are inserted to positions corresponding to the above opposed surfaces in the insertion holes $90h$ of the separator 90 (in FIGS. 13A and 13B, a separator accommodating step).

Subsequently, the metal terminals $30b$ and $30d$ are inserted into the insertion holes $90h$ from the rear-end side of the separator 90 such that the planar portions 312 are interposed between the contact points P2 (the opposed surfaces) and held (in FIGS. 13B and 13C, the metal-terminal holding step). The lead wires 146 are press-fitted to the lead-wire-connecting portions 33 of the metal terminals $30b$ and $30d$ in advance.

Subsequently, the first jig 300 is relatively removed from the separator 90 to the front-end side (lower side) (in FIG. 13D, a jig removing step).

According to the first aspect of the embodiment, when one or more pairs of the metal terminals 20 and 30 are thus installed in the separator 90 such that the contact points P2 (P1) face each other, the planar portions 312 of the first jig 300 are interposed between the contact points P2 (P1). Accordingly, the metal terminals $30b$ and $30d$ (or $20a$ and $20b$, or $30a$ and $30c$) that face each other are inhibited from coming into contact and being entangled with each other, the metal terminals are inhibited from being damaged and deformed, and workability can be improved.

According to the present embodiment, when the separator 90 is accommodated in the first jig 300 in the separator accommodating step in FIG. 13B, the planar portions 312 protrude up to positions nearer than the rear end of the separator 90 to the rear-end side. Thus, at the beginning of the subsequent metal-terminal holding step in which the metal terminals $30b$ and $30d$ (or $20a$ and $20b$, or $30a$ and $30c$) are inserted into the insertion holes $90h$, the metal terminals (contact points P2 and P1) that face each other are isolated from each other by the planar portions 312, and accordingly, the metal terminals can be inhibited from coming into contact and being entangled with each other with certainty.

According to the present embodiment, as illustrated in FIG. 10 and FIG. 12, the first jig 300 includes the straight-line portion $300s$, and the separator 90 includes a second straight-line portion (second restricting member) $90t$ that engages the straight-line portion $300s$. This prevents the separator 90 from rotating in the circumferential direction in the first jig 300 and inhibits the metal terminals from coming into contact and being entangled with each other due to rotation of the separator 90.

According to the present embodiment, the thickness of each planar portion 312 is less than the thickness of the sensing element 10 between the pair of the electrode pads $11a$ and $12a$ (or $11b$ and $12b$, or $11c$ and $12c$) on the front and back surfaces. This inhibits the planar portions 312 from causing the metal terminals to plastically deform by increasing the distance between the metal terminals (contact points P2 and P1) that face each other, and inhibits reliability of the electrical connection from decreasing due to a decrease in the pressure of contact with the electrode pads $11a$ to $12c$ of the sensing element 10, which subsequently occurs.

A method according to a second aspect of the embodiment of the present invention for manufacturing the gas sensor will now be described with reference to FIG. 14 to FIG. 18.

Figure 14:
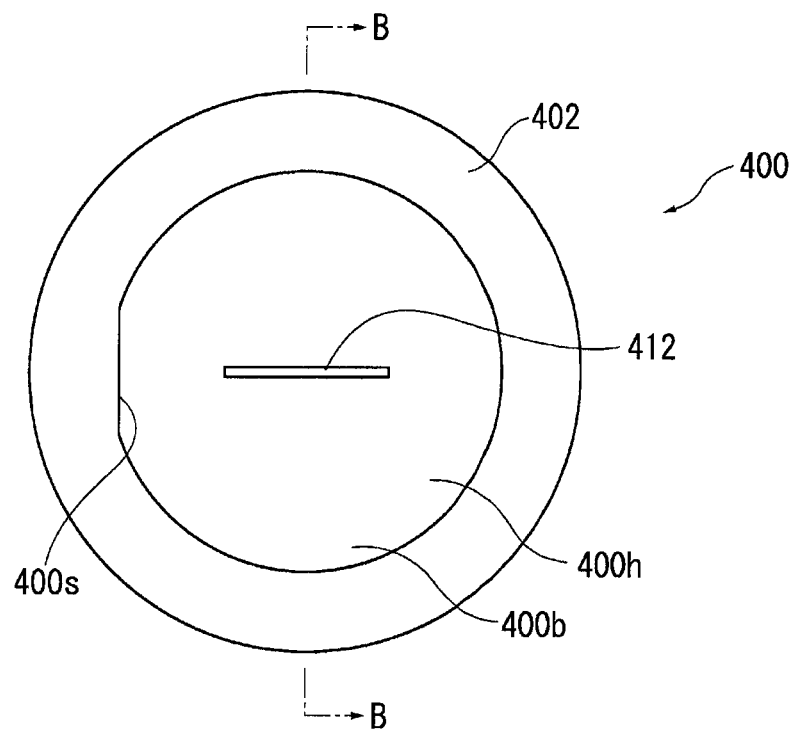
FIG. 14 is a plan view of a second jig used according to a second aspect of the embodiment.
Figure 15:
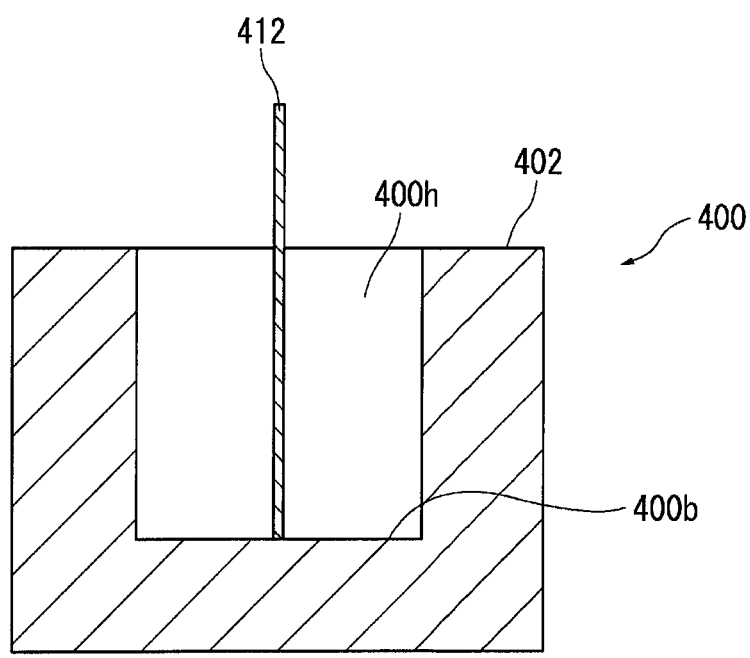
FIG. 15 is a sectional view of FIG. 14 taken along line B-B.
Figure 17:
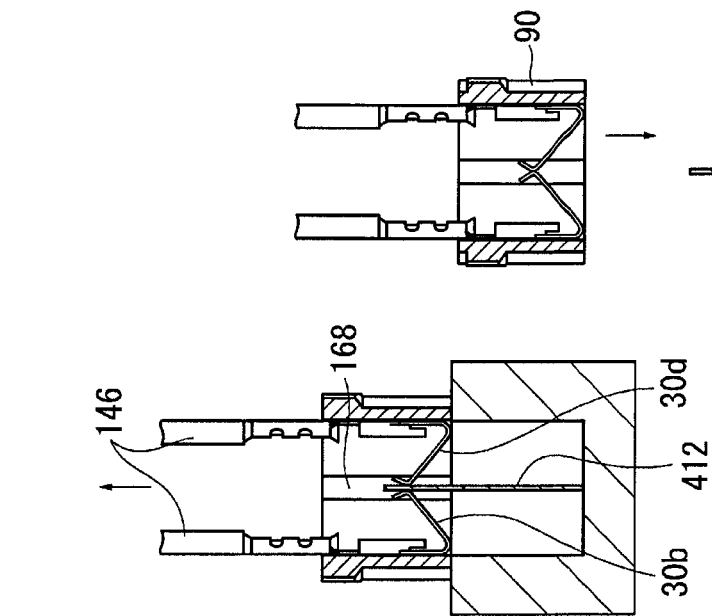
FIGS. 17A-17E are process drawings of a method according to the second aspect of the embodiment for manufacturing the gas sensor.
Figure 18:
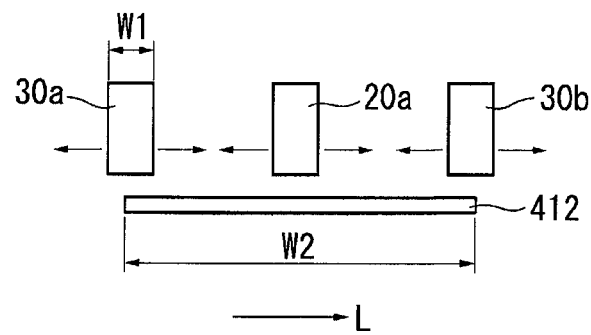
FIG. 18 illustrates a state where the metal terminals shift in arrangement directions with respect to planar portions.
Figure 19:
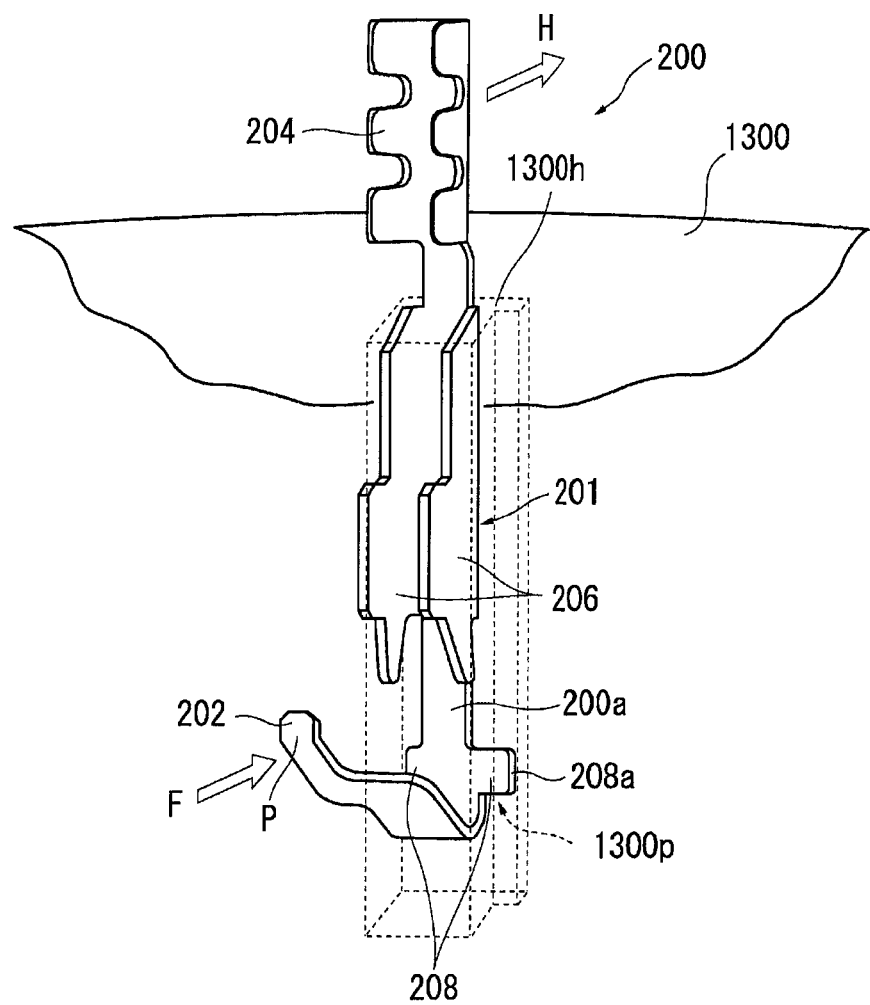
FIG. 19 is a perspective view of a conventional metal terminal.
Figure 20:
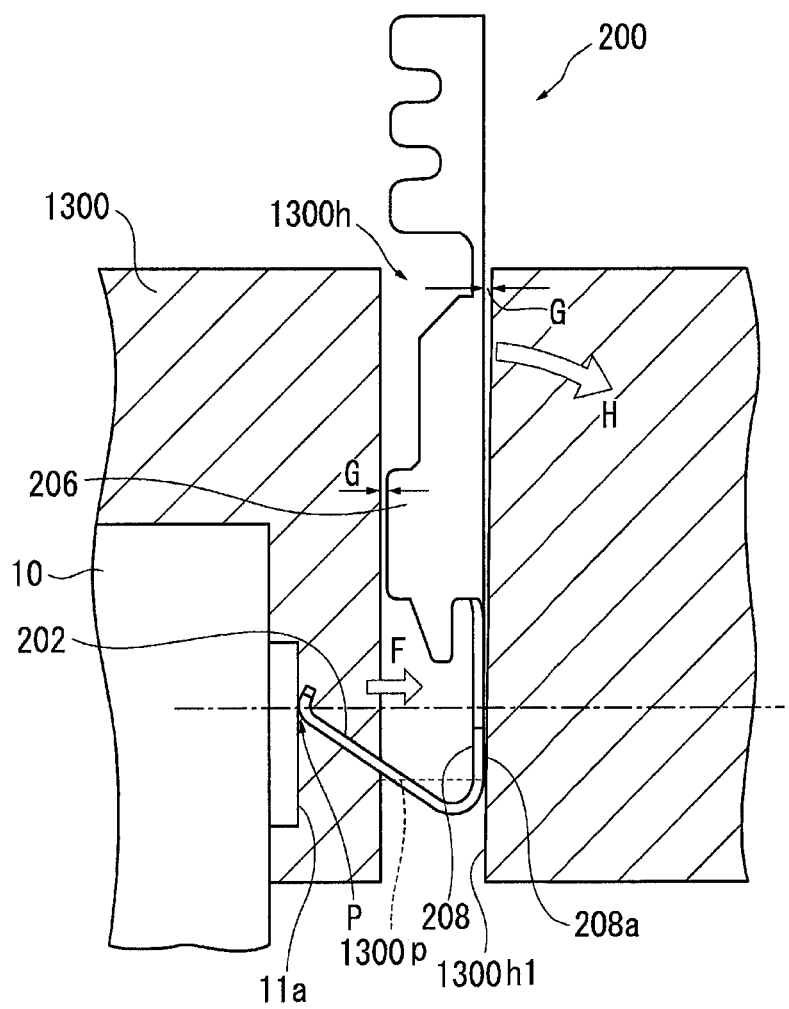
FIG. 20 is a sectional diagram illustrating a state where the conventional metal terminal is held in an insertion hole of a separator.

FIG. 14 is a plan view of a second jig 400 used according to the second aspect of the embodiment. FIG. 15 is a sectional view of FIG. 14 taken along line B-B. FIG. 16 illustrates a state where the metal terminals 20 and 30 are accommodated in the second jig 400. FIGS. 17A-17E are process drawings of the method according to the second aspect of the embodiment for manufacturing the gas sensor. FIG. 18 illustrates a state where the metal terminals 20 and 30 shift in arrangement directions with respect to planar portions 412.

As illustrated in FIG. 14 and FIG. 15, the second jig 400 is formed in a cylindrical shape with a bottom and has, at the center, a cylindrical accommodating space 400h that opens to the upper surface. The two planar portions 412 in a plate shape protrude upward from the center of the bottom surface 400b of the accommodating space 400h. The planar portions 412 are formed at positions corresponding to the insertion hole 90h at the center of the separator 90. The planar portions 412 are formed at positions corresponding to at least the opposed surfaces of a pair of the metal terminals 20a and 20b at the contact points P1 and the opposed surfaces of the other two pairs of the metal terminals 30a to 30d at the contact points P2 (see FIG. 16).

The planar portions 412 protrude up to positions higher than the upper surface 402 of the second jig 400.

A portion around the accommodating space 400h forms a straight-line portion 400s as in the straight-line portion 300s and forms the "first restricting member" that prevents rotation of the separator 90 in the circumferential direction. The separator 90 includes the second straight-line portion (second restricting member) 90t described above.

The second jig 400 and the planar portions 412 can be made of, for example, metal such as stainless steel.

In a metal-terminal holding step of the method according to the second aspect of the embodiment for manufacturing the gas sensor, as illustrated in FIG. 16, the six metal terminals 20a, 20b, and 30a to 30d are inserted in the accommodating space 400h of the second jig 400. At this time, the planar portions 412 are inserted between the opposed surfaces of the metal terminals at the contact points P1 and P2.

As illustrated in FIG. 16, the metal terminals 30a, 20a, and 30b are arranged in a direction L along the main surfaces of the planar portions 412, and the metal terminals 30c, 20b, and 30d are arranged in the same manner on the opposite side with respect to the planar portions 412. The width of each metal terminal at the contact points P1 and P2 is denoted by W1, and the width of the main surfaces of the planar portions 412 is denoted by W2.

As illustrated in FIG. 18, in the case where the total width (3×W1) in the direction (arrangement direction) L in which the metal terminals 30a, 20a, and 30b (or 30c, 20b, and 30d) are arranged is less than W2, even when the metal terminals 30a, 20a, and 30b shift in the arrangement direction L, the metal terminals 30a, 20a, and 30b can be inhabited from passing over the planar portions 412 and coming into contact and being entangled with the metal terminals 30c, 20b, and 30d located on the opposed side with certainty.

As illustrated in a lower part of FIG. 16, in the case where expression 1: GL+GR=W3−W2, GL<W1, and GR<W1 holds where W3 is the maximum width of the insertion holes 90h of the separator 90 in the arrangement direction L, even when the metal terminals 30a and 30b shift in the arrangement direction L, the metal terminals 30a and 30b can be inhabited from passing over the planar portions 412 and coming into contact and being entangled with the metal terminals 30c and 30d located on the opposed side with certainty. The reason is that GL and GR in the expression 1 represent left and right spaces between the planar portions 412 and the insertion holes 90h, and, when the spaces GL and GR are less than the terminal width W1, the metal terminals 30a and 30b cannot reach the opposite side with respect to the planar portions 412. The width of the metal terminals 30a and 30b described herein is donated by W1. However, in the case where the widths of the metal terminals are different, it is preferable that the widths of the terminals closest to the spaces GL and GR be less than the spaces GL and GR.

The detail of the method according to the second aspect of the embodiment for manufacturing the gas sensor will now be described with reference to FIGS. 17A-17E. FIGS. 17A-17E illustrate a pair of the metal terminals 30b and 30d only. However, the same is true for the other two pairs of the metal terminals 20b and 20d, which are into the page and concealed in FIGS. 17A-17E.

The lead wires 146 to be connected to the metal terminals 30b and 30d are inserted into the insertion holes 90h of the separator 90 so as to protrude from the front-end side of the separator 90 (a lead-wire inserting step). Subsequently, the lead-wire-connecting portions 33 of the metal terminals 30b and 30d are press-fitted (electrically connected) to ends of the lead wires 146 (in FIG. 17A, a metal-terminal connecting step).

Subsequently, the metal terminals 30b and 30d are moved from the rear-end side of the second jig 400 and accommodated in the accommodating space 400h at the same positions as the metal terminals 30b and 30d are held in the separator 90, and the planar portions are inserted (interposed) between the contact points P2 (in FIG. 17B, a metal-terminal accommodating step).

Subsequently, an end of the separator 90 is brought into contact with the rear end (upper surface) 402 of the second jig 400 while the lead wires 146 are pulled toward the rear-end side (in FIG. 17C, a separator contacting step). As illustrated in FIG. 17C, the inner diameter D1 of the accommodating space 400h is smaller than the maximum outer diameter D2 of an end portion of the separator 90.

Subsequently, the metal terminals 30b and 30d are inserted from the front-end side of the insertion holes 90h of the separator 90 in contact with the rear end of the second jig 400 and held in the insertion holes 90h (in FIG. 17D, the metal-terminal holding step).

Subsequently, the second jig 400 is relatively removed from the separator 90 to the front-end side (lower side) (in FIG. 17E, a jig removing step).

According to the second aspect of the embodiment, when one or more pairs of the metal terminals 20 and 30 are thus installed in the separator 90 such that the contact points P2 (P1) face each other, the planar portions 412 of the second jig 400 are interposed between the contact points P2 (P1). Accordingly, the metal terminals 30b and 30d (or 20a and 20b, or 30a and 30c) that face each other are inhibited from coming into contact and being entangled with each other, the metal terminals are inhibited from being damaged and deformed, and workability can be improved.

According to the present embodiment, in the separator contacting step in FIG. 17D, the planar portions 412 protrude up to positions nearer than the contact points P2 (P1) to the rear-end side. Thus, when the metal terminals are held in the insertion holes 90h of the separator 90, the metal terminals (contact points P2 (P1)) that face each other are isolated from each other by the planar portions 412, and the metal terminals can be inhibited from coming into contact and being entangled with each other with certainty.

According to the present embodiment, the separator 90 is prevented from rotating in the circumferential direction in the second jig 400 as described above, and the metal terminals can be inhibited from coming into contact and being entangled with each other due to rotation of the separator 90.

It goes without saying that the present invention is not limited to the above embodiments and contains various modifications and equivalents within the spirit and scope of the present invention.

For example, the shape of the metal terminals and the insertion holes of the front-end-side separator is not limited to the above embodiments.

Examples of the gas sensor include an oxygen sensor and a universal gas sensor in addition to a NOx sensor.

The shape of the first jig, the second jig, the separator, and the metal terminals is not limited. The metal terminals may be paired as one pair or two or more pairs.

A pin for positioning may be disposed, as the first restricting member that prevents rotation of the separator in the circumferential direction, on a part of an edge surface of the separator or in the terminal accommodating space of the separator. A plurality of the first restricting members may be provided.

REFERENCE SIGNS LIST 1 gas sensor
10 sensing element
11a to 12c electrode pad
20, 30 metal terminal
20f, 30f flat board portion
21, 31 main body
22, 32 elastic portion
25, 351 rear-end-side restricting portion
29, 352 front-end-side restricting portion
25a, 29a, 35a facing surface
20p burr
90 separator (front-end-side separator)
90h, 90h1, 90h2 insertion hole
90w1, 90w2 wall surface of the insertion hole
90t second restricting member
300 first jig
300h, 400h accommodating space
300b, 400b bottom surface of the accommodating space
300s, 400s first restricting member
312, 412 planar portion
314, 316 metal-terminal restricting member
400 second jig
O axial line
P1, P2 contact point
D1 inner diameter of the accommodating space
D2 maximum outer diameter of an end portion of the separator
L arrangement direction

The invention claimed is:

1. A gas sensor, comprising:
a sensing element that is formed in a plate shape extending in a direction of an axial line and that includes an electrode pad on an outer surface of a rear-end side of the sensing element;
a metal terminal that extends in the direction of the axial line and that is electrically connected to the electrode pad; and
a tubular separator that has an insertion hole into which the metal terminal is inserted and that surrounds a part of the sensing element on the rear-end side, wherein
the metal terminal includes a main body and an elastic portion that is integrally connected to the main body, said elastic portion being folded toward the sensing element and elastically connected to the electrode pad at a predetermined contact point,
the main body includes a front-end-side restricting portion and a rear-end-side restricting portion, both of which further extend from the main body and restrict a movement of the main body by contacting an inner wall surface of the insertion hole when the main body moves in a direction intersecting the direction of the axial line,
the metal terminal abuts on a center of the sensing element in its width direction, and
the inner wall surface of the insertion hole is formed such that it faces the sensing element.

2. The gas sensor according to claim 1, wherein a distance between a front end of the front-end-side restricting portion and a rear end of the rear-end-side restricting portion in the direction of the axial line exceeds a half of a length of the metal terminal in the direction of the axial line inside the insertion hole.

3. The gas sensor according to claim 1 further comprising a burr on the main body that protrudes toward an elastic portion side from surfaces opposite to surfaces that face the wall surface of the separator forming the insertion hole.

4. The gas sensor according to claim 1, wherein the front-end-side restricting portion and the rear-end-side restricting portion are flush with each other in a view from the direction of the axial line.

5. The gas sensor according to claim 1, wherein the insertion hole extends entirely in the direction of the axial line and has a longitudinal length that is longer than a longitudinal length of the flat board portion.

6. A gas sensor, comprising:
a sensing element that is formed in a plate shape extending in a direction of an axial line and that includes an electrode pad on an outer surface of a rear-end side of the sensing element;
a metal terminal that extends in the direction of the axial line and that is electrically connected to the electrode pad; and
a tubular separator that has an insertion hole into which the metal terminal is inserted and that surrounds a part of the sensing element on the rear-end side, wherein
the metal terminal includes a main body and an elastic portion that is integrally connected to the main body, said elastic portion being folded toward the sensing element and elastically connected to the electrode pad at a predetermined contact point,
the main body includes a front-end-side restricting portion and a rear-end-side restricting portion, both of which further extend from the main body and restrict a movement of the main body by contacting an inner wall surface of the insertion hole when the main body moves in a direction intersecting the direction of the axial line,
the metal terminal abuts on an end portion of the sensing element in its width direction, and
the inner wall surface of the insertion hole is formed such that it faces in the same direction as the outer surface of the rear-end side of the sensing element faces.

7. A gas sensor, comprising:
a sensing element that is formed in a plate shape extending in a direction of an axial line and that includes an electrode pad on an outer surface of a rear-end side of the sensing element;
a metal terminal that extends in the direction of the axial line and that is electrically connected to the electrode pad; and
a tubular separator that has an insertion hole into which the metal terminal is inserted and that surrounds a part of the sensing element on the rear-end side, wherein
the metal terminal includes a main body and an elastic portion that is integrally connected to the main body, said elastic portion being folded toward the sensing element and elastically connected to the electrode pad at a predetermined contact point,
the main body includes a front-end-side restricting portion and a rear-end-side restricting portion, both of which further extend from the main body and restrict a movement of the main body by contacting an inner wall surface of the insertion hole when the main body moves in a direction intersecting the direction of the axial line, and
the separator has a rear-end facing surface with which a part of the main body is configured to contact when the metal terminal is inserted into the insertion hole so that an axial movement of the main body is restricted.

8. The gas sensor according to claim 7, wherein the front-end-side restricting portion is the part of the main body that contacts the rear-end facing surface.

9. The gas sensor according to claim 7, wherein
the main body further contains a position-restricting portion formed at a forward end side with respect to the front-end-side restricting portion, and
the position-restricting portion is the part that contacts the rear-end facing surface.

\* \* \* \* \*